US008817948B2

(12) United States Patent
Kusunoki

(10) Patent No.: US 8,817,948 B2
(45) Date of Patent: Aug. 26, 2014

(54) RADIOGRAPHIC IMAGING APPARATUS AND RADIOGRAPHIC IMAGING SYSTEM

(75) Inventor: Tetsuro Kusunoki, Kanagawa (JP)

(73) Assignee: Fujifilm Corporation, Tokyo (JP)

( * ) Notice: Subject to any disclaimer, the term of this patent is extended or adjusted under 35 U.S.C. 154(b) by 827 days.

(21) Appl. No.: 12/929,426

(22) Filed: Jan. 24, 2011

(65) Prior Publication Data
US 2011/0235776 A1    Sep. 29, 2011

(30) Foreign Application Priority Data
Mar. 29, 2010  (JP) ................................. 2010-076014

(51) Int. Cl.
*A61B 6/04* (2006.01)
*A61B 6/02* (2006.01)
*A61B 6/00* (2006.01)
*H04N 13/04* (2006.01)
*H04N 13/02* (2006.01)

(52) U.S. Cl.
CPC ............... *A61B 6/462* (2013.01); *A61B 6/4291* (2013.01); *H04N 13/0443* (2013.01); *H04N 13/0434* (2013.01); *H04N 13/0221* (2013.01); *A61B 6/463* (2013.01); *A61B 6/502* (2013.01); *A61B 6/022* (2013.01); *H04N 13/0253* (2013.01)
USPC .............................................. 378/37; 378/41

(58) Field of Classification Search
USPC ..................................................... 378/37, 41
See application file for complete search history.

(56) References Cited

U.S. PATENT DOCUMENTS

| 5,212,637 | A | 5/1993 | Saxena | |
|---|---|---|---|---|
| 6,760,469 | B1 | 7/2004 | Berestov et al. | |
| 7,123,684 | B2 * | 10/2006 | Jing et al. | 378/37 |
| 7,212,606 | B2 * | 5/2007 | Souchay et | 378/37 |
| 7,443,950 | B2 * | 10/2008 | Sendai | 378/37 |
| 7,453,979 | B2 * | 11/2008 | Sendai | 378/23 |
| 7,463,713 | B2 * | 12/2008 | Mertelmeier | 378/22 |

(Continued)

FOREIGN PATENT DOCUMENTS

| DE | 3520917 | 12/1986 |
|---|---|---|
| JP | H05501513 A | 3/1993 |

(Continued)

OTHER PUBLICATIONS

Notice of Reasons for Rejection, issued by the Japanese Patent Office on Jul. 16, 2013 in JP2010-076014, which corresponds to the present application.

(Continued)

*Primary Examiner* — Allen C. Ho
(74) *Attorney, Agent, or Firm* — Jean C. Edwards, Esq.; Edwards Neils PLLC

(57) ABSTRACT

A radiographic imaging apparatus is provided with a generation unit, a radiation source, a moving unit, and an imaging control unit. The generation unit captures radiographic images based on beams of radiation that have been transmitted through an imaging target site and with which an imaging surface has been individually irradiated and generates sets of image information representing the captured radiographic images. The moving unit moves the radiation source such that irradiation with the beams of radiation is possible from different directions including a front direction. The imaging control unit controls the moving unit such that, in a case where the radiographic imaging apparatus performs stereo imaging, the imaging surface is irradiated with the beams of radiation from the front direction and from a direction of a predetermined angle.

7 Claims, 14 Drawing Sheets

(56) References Cited

U.S. PATENT DOCUMENTS

| | | | |
|---|---|---|---|
| 7,496,219 B2* | 2/2009 | Okada | 382/128 |
| 7,545,907 B2* | 6/2009 | Stewart et al. | 378/37 |
| 7,577,282 B2* | 8/2009 | Gkanatsios et al. | 382/128 |
| 7,693,254 B2* | 4/2010 | Muller et al. | 378/37 |
| 7,697,661 B2* | 4/2010 | Souchay et al. | 378/37 |
| 7,778,388 B2* | 8/2010 | Sendai | 378/22 |
| 7,831,296 B2* | 11/2010 | DeFreitas et al. | 600/427 |
| 7,885,379 B2* | 2/2011 | Meer et al. | 378/37 |
| 7,916,914 B2* | 3/2011 | Heinlein et al. | 382/128 |
| 8,031,834 B2* | 10/2011 | Ludwig et al. | 378/22 |
| 8,094,778 B2* | 1/2012 | Sendai | 378/41 |
| 8,184,770 B2* | 5/2012 | Fischer et al. | 378/62 |
| 8,363,050 B2* | 1/2013 | Ludwig et al. | 345/419 |
| 2006/0050137 A1 | 3/2006 | Okada | |
| 2010/0027859 A1 | 2/2010 | Heinlein et al. | |
| 2010/0104166 A1* | 4/2010 | Hall et al. | 382/132 |

FOREIGN PATENT DOCUMENTS

| | | | |
|---|---|---|---|
| JP | 10-80418 | 3/1998 | |
| JP | 2004-97830 | 4/2004 | |
| JP | 2004097830 A | 4/2004 | |
| JP | 2007195663 A | 8/2007 | |
| JP | 2007-229201 A | 9/2007 | |
| WO | WO 2009/076303 A2 | 6/2009 | |
| WO | WO 2009/080379 A1 * | 7/2009 | A61B 6/00 |

OTHER PUBLICATIONS

Chinese Office Action issued by State Intellectual Property Office on Mar. 4, 2014 in connection with corresponding Chinese Patent Application No. 201110033182.9.

* cited by examiner

BACK ← → FRONT

RADIOGRAPHIC IMAGING APPARATUS AND RADIOGRAPHIC IMAGING SYSTEM

CROSS-REFERENCE TO RELATED APPLICATION

This application claims priority under 35 USC 119 from Japanese Patent Application No. 2010-076014 filed on Mar. 29, 2010, the disclosure of which is incorporated by reference herein.

BACKGROUND OF THE INVENTION

1. Field of the Invention

The present invention pertains to a radiographic imaging apparatus and a radiographic imaging system and particularly relates to a radiographic imaging apparatus and a radiographic imaging system that perform stereo imaging.

2. Description of the Related Art

Conventionally, radiographic imaging apparatus that perform radiographic imaging for medical diagnosis have been known. Examples of this type of radiographic imaging apparatus include mammography machines that image the breasts of subjects for the early detection of breast cancer and so forth.

In an examination using a mammography machine, the right and left breasts of an subject are individually imaged. It is common for the reader to have the radiographic images of the right and left breasts that have been captured displayed side-by-side such that their chest wall sides face each other and to compare the right and left breasts. Japanese Patent Application Laid-Open (JP-A) No. 2004-97830 discloses a technology by which one of the radiographic images of the right and left breasts is rotated 180 degrees, the radiographic images of the right and left breasts are synthesized such that the edges of their chest sides are brought together, and a synthesized image in which the radiographic images have been synthesized is displayed.

Radiographic images obtained by imaging with radiographic imaging apparatus are two-dimensional images, so it is difficult to judge the three-dimensional distribution of lesions and so forth.

As a technique for improving diagnostic accuracy, there has been proposed a method of performing stereo imaging, where an imaging target site of a subject is irradiated twice with beams of radiation at predetermined parallactic angles with respect to capture radiographic images thereof, and allowing the two radiographic images that have been captured to be viewed individually by the right eye and the left eye of the reader so that the reader may stereoscopically view the radiographic images.

By mutually interchanging the images to reverse the images viewed by the right eye and the left eye, or by inverting right and left in each of the two radiographic images, or by rotating 180 degrees each of the two radiographic images, the two radiographic images that have been captured by stereo imaging appear such that the projecting directions of the stereoscopically viewed images are inverted and the images are being viewed from opposite directions.

In mammography, stereo imaging is performed with respect to the right and left breasts to capture two radiographic images each of the right breast and the left breast, and the radiographic images of the right and left breasts that have been captured are stereoscopically inspected while being compared. In a case where the two radiographic images of either one of the right breast or the left breast are rotated 180 degrees and synthesized with the other two radiographic images, the directions in which the right breast and the left breast project end up becoming opposite in the stereoscopically viewed images as a result of the former two radiographic images having been rotated 180 degrees.

JP-A No. 10-80418 discloses a technology by which, in a case where right and left directions of displayed images have been inverted, right and left images are mutually interchanged in conjunction with this such that an appropriate sense of depth is always imparted.

By using the technology described in JP-A No. 10-80418 to rotate 180 degrees the two radiographic images of either one of the right breast or the left breast in order to put together their chest sides, mutually interchange the two radiographic images to reverse the images viewed by the right eye and the left eye, or invert right and left in the two radiographic images, the directions in which the right breast and the left breast project can be made the same in the stereoscopically viewed images.

SUMMARY OF THE INVENTION

The present invention has been made in view of the above circumstances and provides a radiographic imaging apparatus and a radiographic imaging system.

According to an aspect of the invention, there is provided a radiographic imaging apparatus including: a generation unit that captures radiographic images based on beams of radiation that have been transmitted through an imaging target site and with which an imaging surface has been individually irradiated and generates sets of image information representing the captured radiographic images; a radiation source that irradiates the imaging surface with the beams of radiation; a moving unit that moves the radiation source such that irradiation with the beams of radiation is possible from different directions including a front direction in which the radiation source directly faces the imaging surface; and an imaging control unit that controls the moving unit such that, in a case where the radiographic imaging apparatus performs stereo imaging, the imaging surface is irradiated with the beams of radiation from the front direction and from a direction of a predetermined angle with respect to the front direction.

BRIEF DESCRIPTION OF THE DRAWINGS

Preferred embodiments of the present invention will be described in detail based on the following figures, wherein.

DETAILED DESCRIPTION OF THE INVENTION

Figure 1:
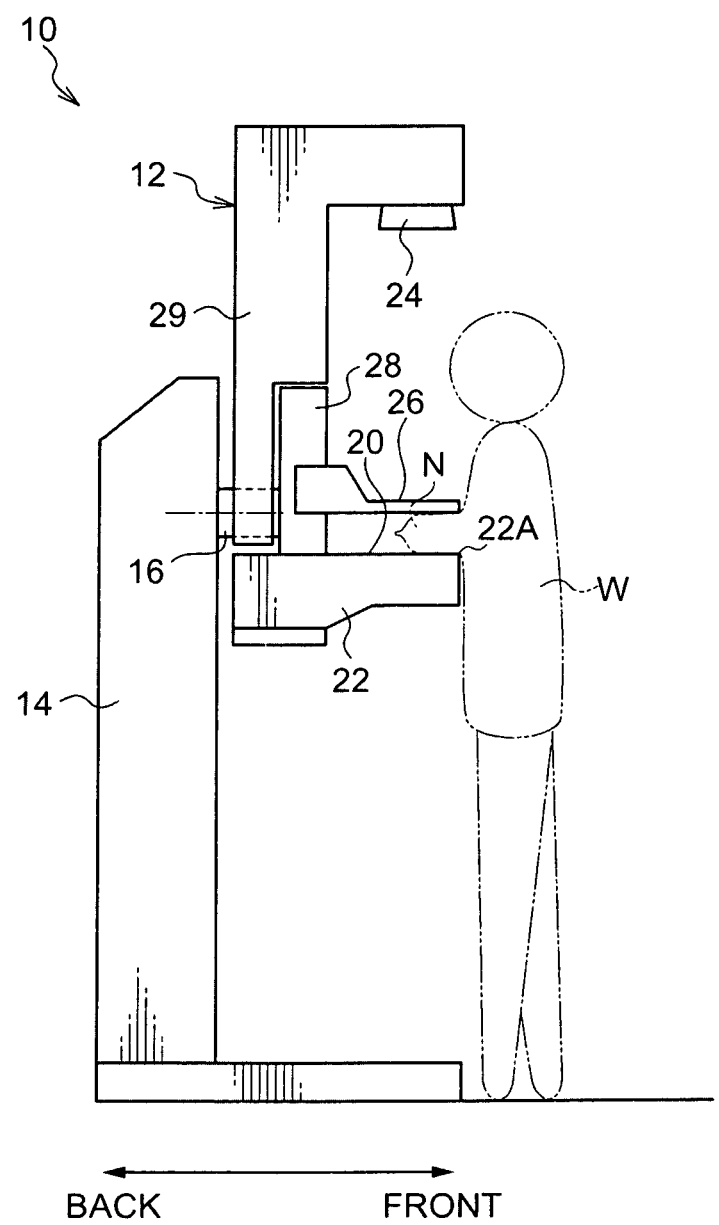
FIG. 1 is a side view showing the configuration of an imaging apparatus pertaining to the embodiments.

In a case where the radiation source is tilted with respect to the imaging surface on which radiographic images are captured when the radiographic imaging apparatus performs stereo imaging, the beam of radiation is made incident diagonally with respect to the imaging surface, and the image quality of the captured radiographic image deteriorates as compared to a case where the beam of radiation is made incident from a perpendicular direction with respect to the imaging surface. Particularly in a case where a grid is disposed in the imaging surface, the beam of radiation that has been made incident diagonally ends up being kicked by the grid, and the image quality of the captured radiographic image drops.

For this reason, in a case where radiographic images that have been captured by stereo imaging are stereoscopically viewed, the image quality deteriorates.

The present invention provides a radiographic imaging device and a radiographic imaging system with which an imaging target site can be stereoscopically observed while image quality deterioration in a case where radiographic images that have been captured by stereo imaging are stereoscopically viewed is suppressed.

According to a first aspect of the present invention, there is provided a radiographic imaging apparatus including: a generation unit that captures radiographic images based on beams of radiation that have been transmitted through an imaging target site and with which an imaging surface has been individually irradiated and generates sets of image information representing the captured radiographic images; a radiation source that irradiates the imaging surface with the beams of radiation; a moving unit that moves the radiation source such that irradiation with the beams of radiation is possible from different directions including a front direction in which the radiation source directly faces the imaging surface; and an imaging control unit that controls the moving unit such that, in a case where the radiographic imaging apparatus performs stereo imaging, the imaging surface is irradiated with the beams of radiation from the front direction and from a direction of a predetermined angle with respect to the front direction.

In this manner, according to the invention pertaining to the first aspect, in a case where the radiographic imaging apparatus performs stereo imaging, the imaging surface is irradiated with the beams of radiation from the front direction in which the radiation source directly faces the imaging surface and from the direction of the predetermined angle with respect to the front direction, so in a case where radiographic images that have been captured by stereo imaging are stereoscopically viewed, the imaging target site can be stereoscopically observed while image quality deterioration is suppressed.

According to a second aspect of the present invention, in the first aspect, the imaging target site may be breasts, in a case where the radiographic imaging apparatus performs stereo imaging of a right breast and a left breast, the imaging control unit may control the moving unit such that the imaging surface is irradiated with the beams of radiation from the front direction and from the direction of the predetermined angle, and the radiographic imaging apparatus further may include a display control unit that performs control such that radiographic images in which a right breast and a left breast have been individually stereo-imaged are displayed side-by-side at a display unit such that their chest sides meet and such that the directions in which the right breast and the left breast project are the same when stereoscopically viewed, wherein the display unit displays images so as to allow the images to be viewed individually by a right eye and a left eye such that stereoscopic viewing is possible.

According to a third aspect of the present invention, in the second aspect, the imaging control unit may set the predetermined angle in opposite directions with respect to the front direction when imaging the right breast and when imaging the left breast.

According to a fourth aspect of the present invention, in the second or third aspect, the display control unit may perform control such that two radiographic images, in which either one of the right breast or the left breast has been stereo-imaged, are rotated 180 degrees, the two radiographic images are mutually interchanged, and a synthesized image is displayed in which the two radiographic images and two other radiographic images in which the other breast has been stereo-imaged are arranged side-by-side and synthesized such that their chest sides meet.

According to a fifth aspect of the present invention, there is provided a radiographic imaging system including: a) a radiographic imaging apparatus which includes a generation unit that captures radiographic images based on beams of radiation that have been transmitted through an imaging target site and with which an imaging surface has been individually irradiated and generates sets of image information representing the captured radiographic images, a radiation source that irradiates the imaging surface with the beams of radiation, a moving unit that moves the radiation source such that irradiation with the beams of radiation is possible from different directions including a front direction in which the radiation source directly faces the imaging surface, and an imaging control unit that controls the moving unit such that, in a case where the radiographic imaging apparatus performs stereo imaging, the imaging surface is irradiated with the beams of radiation from the front direction and from a direction of a predetermined angle with respect to the front direction; b) a display device that displays images so as to allow the images to be viewed individually by a right eye and a left eye such that stereoscopic viewing is possible; and c) a display control unit that performs control such that radiographic images in which a right breast and a left breast have been individually stereo-imaged are displayed side-by-side such that their chest sides meet and such that the directions in which the right breast and the left breast project are the same when stereoscopically viewed.

Thus, the invention pertaining to the fifth aspect acts in the similar manner as the invention pertaining to the first aspect, so the right breast and the left breast can be stereoscopically observed while image quality deterioration in a case where radiographic images that have been captured by stereo imaging are stereoscopically viewed is suppressed.

According to the present invention, an imaging target site can be stereoscopically observed while image quality deterioration in a case where radiographic images that have been captured by stereo imaging are stereoscopically viewed is suppressed.

First Exemplary Embodiment

A case where the present invention is applied to a radiographic imaging system that performs stereo imaging of breasts and performs stereo display of captured radiographic images will be described below with reference to the drawings.

First, a radiographic imaging apparatus 10 that captures radiographic images will be described with reference to FIG. 1 to FIG. 3.

The radiographic imaging apparatus 10 pertaining to the present embodiment is an apparatus that uses radiation (e.g., X-rays) to image breasts N of a subject W in a standing state where the subject W is standing. The radiographic imaging apparatus 10 is, for example, called a mammography machine. Hereinafter, the near side of the radiographic imaging apparatus 10 that is near the subject W in a case where the subject W faces the radiographic imaging apparatus 10 at the time of imaging will be described as the apparatus front side of the radiographic imaging apparatus 10, the far side of the radiographic imaging apparatus 10 that is away from the subject W in a case where the subject W faces the radiographic imaging apparatus 10 at the time of imaging will be described as the apparatus back side of the radiographic imaging apparatus 10, and the left-right direction of the subject W in a case where the subject W faces the radiographic imaging apparatus 10 will be described as the apparatus left-right direction of the radiographic imaging apparatus 10 (see the arrows in FIG. 2).

As shown in FIG. 1, the radiographic imaging apparatus 10 is equipped with a measuring portion 12, which is disposed on the apparatus front side and is generally shaped like a square C when seen from the side, and a stand portion 14, which supports the measuring portion 12 from the apparatus back side.

Figure 2:
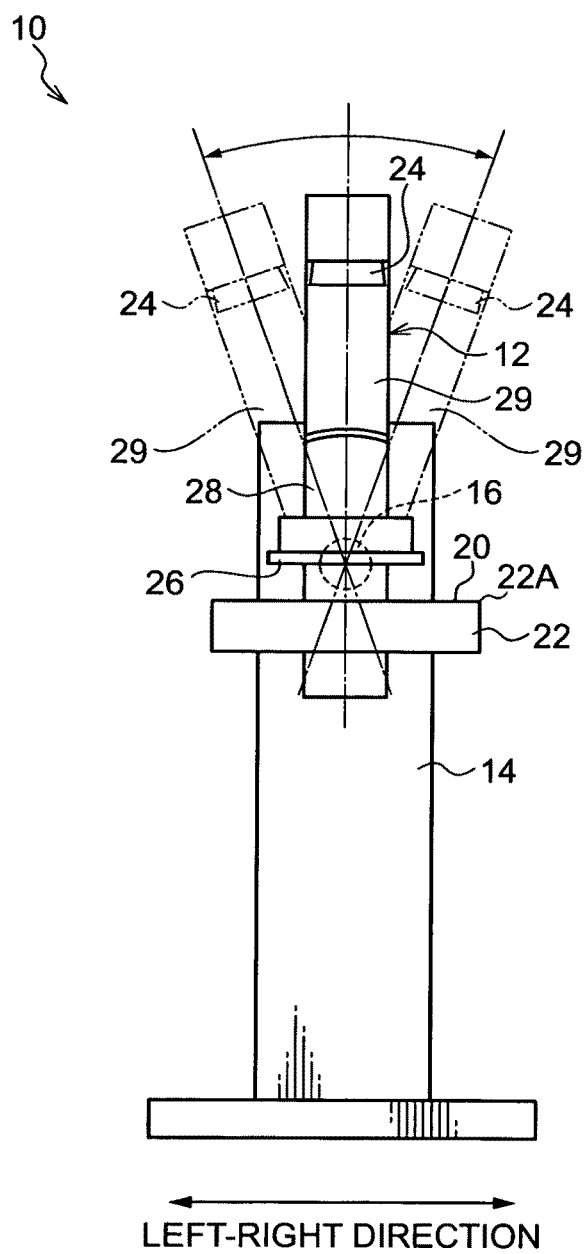
FIG. 2 is a front view showing the configuration of the imaging apparatus pertaining to the embodiments at the time of CC imaging.

As shown in FIG. 1 and FIG. 2, the measuring portion 12 is equipped with an object table 22 on which is formed a planar imaging surface 20 that touches breasts N of the subject W in the standing state, a compression plate 26 that presses the breasts N against the imaging surface 20, and a holding portion 28 that holds the object table 22 and the compression plate 26.

The measuring portion 12 is also equipped with a radiation irradiation unit 24, in which a radiation source 30 (see FIG. 5) such as a tube is disposed and which irradiates the imaging surface 20 with a beam of radiation from that radiation source 30, and a support portion 29, which is separate from the holding portion 28 and supports the radiation irradiation unit 24.

In the measuring portion 12, there is disposed a rotating shaft 16 that is supported so as to be rotatable in the stand portion 14. The rotating shaft 16 is fixed with respect to the support portion 29, so that the rotating shaft 16 and the support portion 29 integrally rotate.

The rotating shaft 16 is configured so as to be switchable between a state where it is coupled to and integrally rotates with the holding portion 28 and a state where it is decoupled from the support portion 28 and idles. Specifically, gears are disposed in the rotating shaft 16 and in the holding portion 28, and the rotating shaft 16 is configured to switch between a state where these gears are engaged with each other and a state where these gears are disengaged from each other.

Various mechanical elements may also be used to switch between the state where the rotational force of the rotating shaft 16 is transmitted to the holding portion 28 and the state where the rotational force of the rotating shaft 16 is not transmitted to the holding portion 28.

The holding portion 28 holds the object table 22 such that the imaging surface 20 and the radiation irradiation unit 24 are separated by a predetermined distance and slidably holds the compression plate 26 such that the distance between the compression plate 26 and the imaging surface 20 is variable.

The radiographic imaging apparatus 10 pertaining to the present embodiment is configured as an apparatus that can perform at least both CC (craniocaudal) imaging and MLO (mediolateral oblique) imaging of the breasts N. FIG. 1 and FIG. 2 show the posture of the radiographic imaging apparatus 10 at the time of CC imaging, and FIG. 3 shows the posture of the radiographic imaging apparatus 10 at the time of MLO imaging.

As shown in FIG. 1, at the time of CC imaging, the posture of the holding portion 28 is adjusted to a state where the imaging surface 20 faces up and the posture of the support portion 29 is adjusted to a state where the radiation irradiation unit 24 is positioned over the imaging surface 20. Thus, the breast N is irradiated with a beam of radiation from the radiation irradiation unit 24 from the cranial side to the caudal side of the subject W in the standing state, and CC (craniocaudal) imaging is performed.

Figure 3:
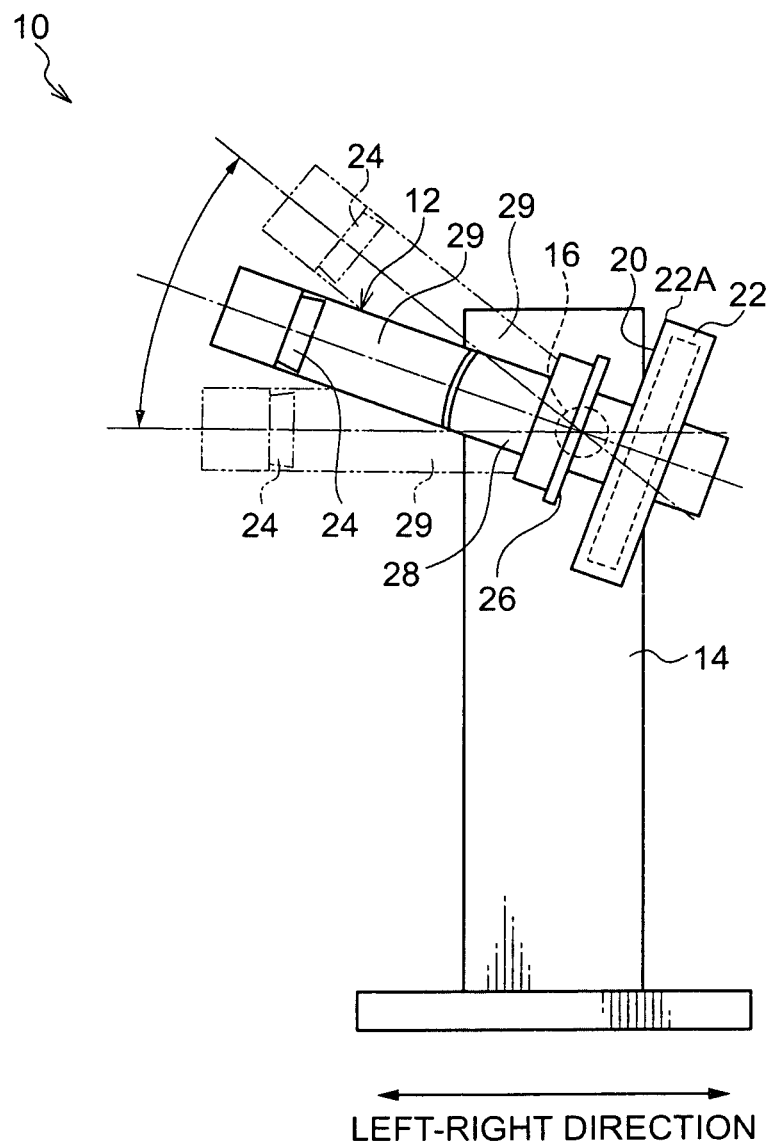
FIG. 3 is a front view showing the configuration of the imaging apparatus pertaining to the embodiments at the time of MLO imaging.

At the time of MLO imaging, as shown in FIG. 3, usually the posture of the holding portion 28 is adjusted to a state where the object table 22 has been rotated 45° or more and less than 90° as compared to at the time of CC imaging and the armpit of the subject W is positioned so as to rest on a side wall corner portion 22A on the apparatus front side of the object table 22. Thus, the breast N is irradiated with a beam of radiation from the radiation irradiation unit 24 from the axial center side of the torso of the subject W outward, and MLO (mediolateral oblique) imaging is performed.

As shown in FIG. 2 and FIG. 3, in a case where the radiographic imaging apparatus 10 performs stereo imaging, the rotating shaft 16 idles with respect to the holding portion 28 so that the object table 22 and the compression plate 26 do not move, and just the radiation irradiation unit 24 moves in an arc as a result of the support portion 29 rotating.

In this manner, by rotating only the radiation irradiation unit 24, it becomes possible to position the radiation irradiation unit 24 in various angles with respect to the imaging surface 20, and the imaging surface 20 can be irradiated with a beam of radiation from various directions including a front direction in which the radiation irradiation unit 24 directly faces the imaging surface 20.

Figure 4:
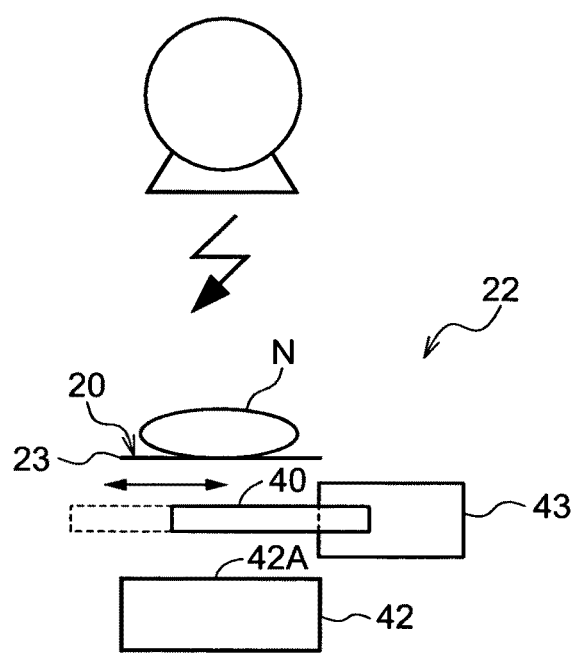
FIG. 4 is a configuration diagram showing the general configuration of an object table pertaining to the embodiments.

FIG. 4 shows the general configuration of the object table 22.

As shown in FIG. 4, the object table 22 is equipped with a top plate 23 on which is formed the imaging surface 20 on which the breast N is placed at the time of imaging, a radiation detector 42 such as a flat panel detector (FPD) on which a sensor surface 42A is placed so as to oppose the top plate 23 and which directly converts the radiation received by the sensor surface 42A into digital data, a grid 40 that is placed on the top plate 23 side of the sensor surface 42A and removes the scatter component of the radiation that arises when the radiation is transmitted through the breast N, and a moving mechanism 43 that reciprocally moves the grid 40 in a plane in line with the sensor surface 42A.

In the grid 40, absorption portions (so-called foil) whose radiation absorption rate is large and transmission portions whose radiation absorption rate is small are alternately disposed at a predetermined pitch, and the grid 40 removes scattered radiation by using the absorption portions to absorb the radiation that scatters inside the breast N and is made diagonally incident on the grid 40.

The beam of radiation that has been radiated from the radiation irradiation unit 24 is transmitted through the breast N, is further transmitted through the grid 40, and reaches the radiation detector 42. In the radiation detector 42, plural sensor portions having sensitivity to the radiation are two-dimensionally disposed in the sensor surface 42A, and the radiation detector 42 captures the radiographic image that has been received by the sensor surface 42A.

The moving mechanism 43 has a built-in motor, is configured as a mechanism that uses the driving force of the motor to reciprocally move the grid 40 in the horizontal direction with respect to the sensor surface 42A, and is configured such that it can change the cycle in which it reciprocally moves the grid 40. As the drive source that reciprocally moves the grid 40, another drive unit such as a piezoelectric element may also be used.

Figure 5:
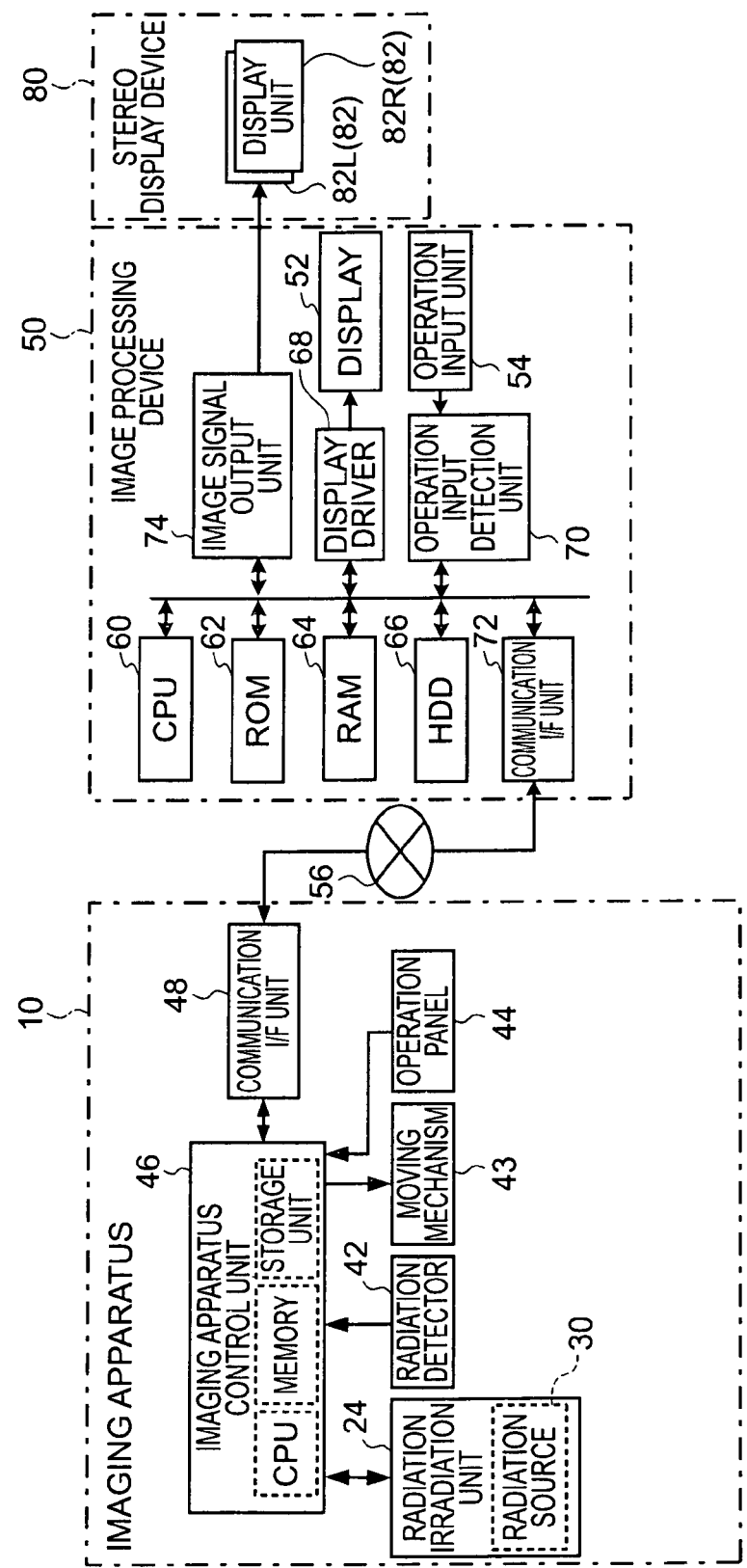
FIG. 5 is a block diagram showing the configuration of a radiographic imaging system pertaining to the embodiments.

FIG. 5 is a block diagram showing the detailed configuration of a radiographic imaging system 5 pertaining to the present embodiment.

The radiographic imaging system 5 is equipped with the radiographic imaging apparatus 10, an image processing device 50 that performs reconfiguration of the captured radiographic images, and a stereo display device 80 that performs stereo display of the reconfigured images.

The radiographic imaging apparatus 10 is further equipped with an operation panel 44 to which various types of operation information, such as exposure conditions and posture information, and various types of operation instructions are inputted, an imaging apparatus control unit 46 that controls the operation of the entire apparatus, and a communication I/F unit 48 that is connected to a network 56 such as a LAN and transmits various types of information to and receives various types of information from other devices connected to the network 56.

The imaging apparatus control unit 46 is equipped with a CPU, a memory including a ROM and a RAM, and a non-volatile storage unit comprising an HDD or a flash memory. The imaging apparatus control unit 46 is connected to the radiation irradiation unit 24, the radiation detector 42, the moving mechanism 43, the operation panel 44, and the communication I/F unit 48. Consequently, the imaging apparatus control unit 46 can perform control of the radiation of the beam of radiation from the radiation irradiation unit 24, control of the imaging operation of the radiation detector 42, control of the operation of the reciprocal movement of the grid 40 via the moving mechanism 43, and control of the transmission of various types of information to and the reception of various types of information from other devices via the communication I/F unit 48. The imaging apparatus control unit 46 can grasp operation instructions that have been inputted with respect to the operation panel 44.

The exposure conditions that have been designated on the operation panel 44 include information such as the tube voltage, the tube current, and the irradiation time, and the posture information includes information indicating whether the imaging posture is CC imaging or MLO imaging. The various types of operation information, such as the exposure conditions and the posture information, and the various types of operation instructions may also be obtained from another control device.

The image processing device 50 is configured as a server computer and is equipped with a display 52, which displays operation menus and various types of information, and an operation input unit 54, which is configured to include plural keys and to which various types of information and operation instructions are inputted.

The image processing device 50 is equipped with a CPU 60 that controls the operation of the entire device, a ROM 62 in which various types of programs and so forth including a control program are stored beforehand, a RAM 64 that temporarily stores various types of data, an HDD 66 that stores and holds various types of data, a display driver 68 that controls the display of various types of information on the display 52, an operation input detection unit 70 that detects states of operation with respect to the operation input unit 54, a communication I/F unit 72 that is connected to the radiographic imaging apparatus 10 via the network 56 and transmits various types of information to and receives various types of information from the radiographic imaging apparatus 10, and an image signal output unit 74 that outputs image signals with respect to the stereo display device 80 via a display cable.

The CPU 60, the ROM 62, the RAM 64, the HDD 66, the display driver 68, the operation input detection unit 70, the communication I/F unit 72, and the image signal output unit 74 are interconnected via a system bus. Consequently, the CPU 60 can access the ROM 62, the RAM 64, and the HDD 66. The CPU 60 can perform control of the display of various types of information on the display 52 via the display driver 68, control of the transmission of various types of information to and the reception of various types of information from the radiographic imaging apparatus 10 via the communication I/F unit 72, and control of images displayed on the stereo display device 80 via the image signal output unit 74. The CPU 60 can grasp states of operation by a user with respect to the operation input unit 54 via the operation input detection unit 70.

Figure 6:
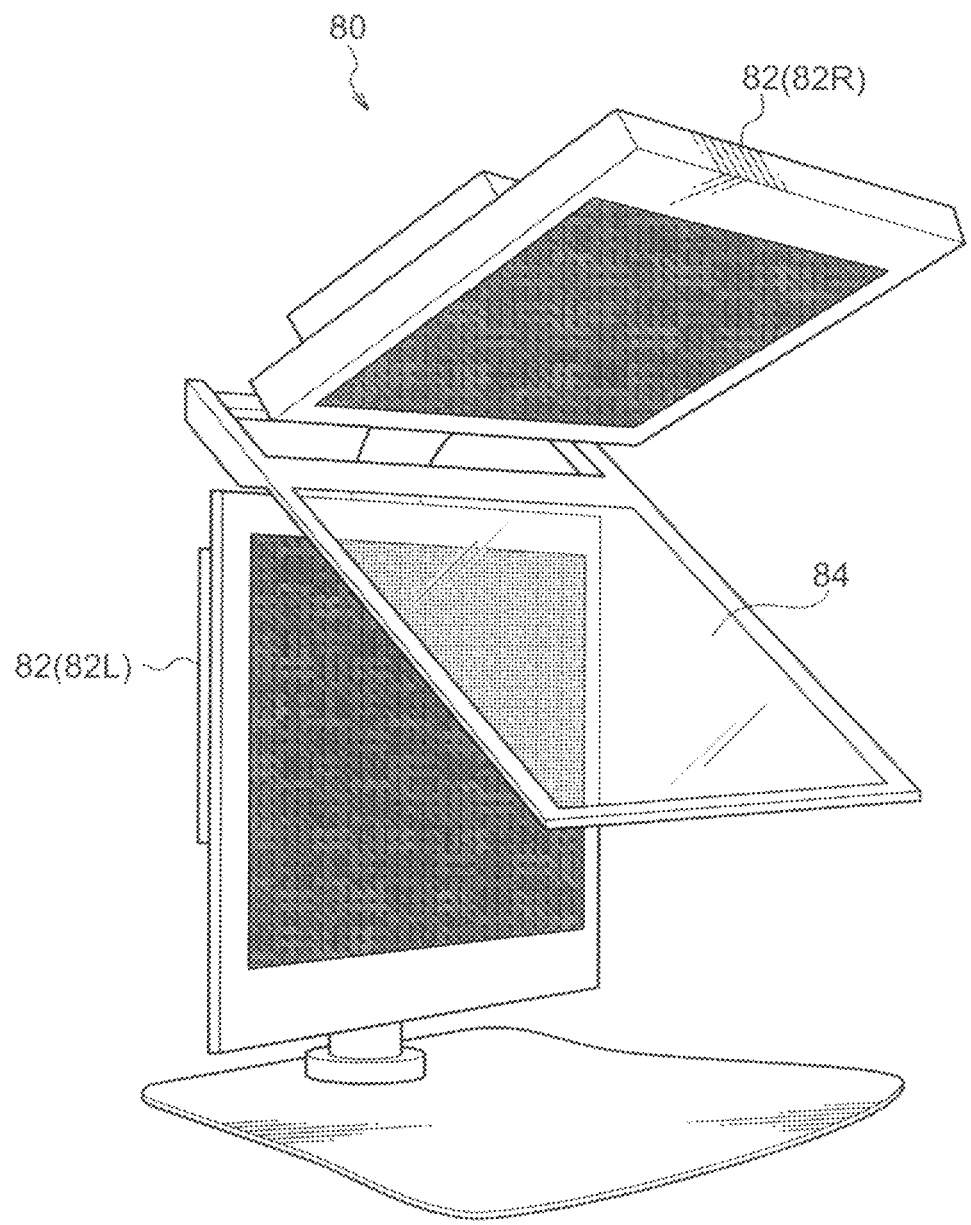
FIG. 6 is a perspective view showing the configuration of a stereo display device pertaining to the embodiments.

FIG. 6 shows one example of the configuration of the stereo display device 80 pertaining to the present embodiment.

As shown in FIG. 6, the stereo display device 80 has two display units 82 that are placed vertically side-by-side, and the upper display unit 82 is tilted forward and fixed. The display light polarization directions of the two display units 82 are orthogonal. The upper display unit 82 is configured as a display unit 82R that displays images for the right eye, and the lower display unit 82 is configured as a display unit 82L that displays images for the left eye. Between these display units 82L and 82R, there is disposed a beam splitter mirror 84 that transmits the display light from the display unit 82L and reflects the display light from the display unit 82R. The beam splitter mirror 84 is fixed with its angle adjusted such that the image displayed on the display unit 82L and the image displayed on the display unit 82R become superimposed when a reader such as a doctor views the stereo display device 80 from the front.

Figure 7:
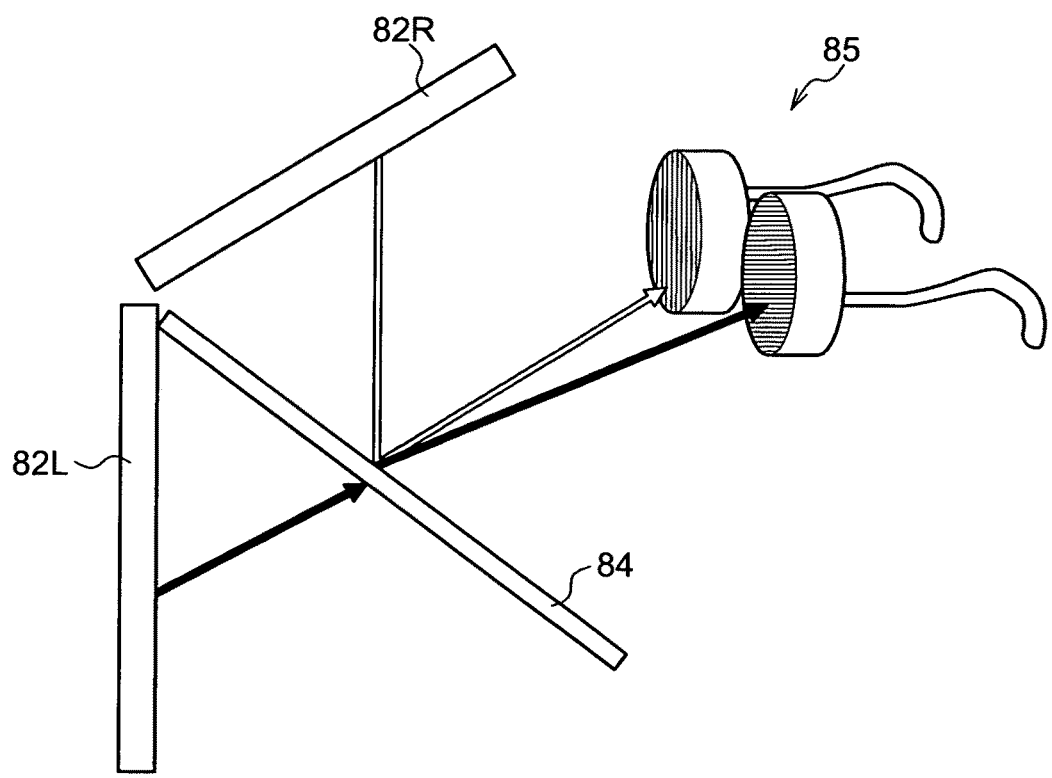
FIG. 7 is a diagram showing a case where images displayed by the stereo display device pertaining to the embodiments are stereoscopically viewed.

As shown in FIG. 7, by wearing polarization glasses 85 whose polarization directions are made orthogonal in the right lens and the left lens and viewing the stereo display device 80, the reader can separately view with the right eye and the left eye the image displayed on the display unit 82L and the image displayed on the display unit 82R.

Next, the action of the radiographic imaging system 5 pertaining to the present embodiment will be described.

In a case where the radiographic imaging apparatus 10 performs stereo imaging to capture radiographic images, the exposure conditions and the posture information are inputted with respect to the operation panel 44 of the radiographic imaging apparatus 10.

In the radiographic imaging apparatus 10, in a case where the imaging posture that has been designated in the posture information is CC imaging, as shown in FIG. 2, the posture of the holding portion 28 is adjusted to a state where the imaging surface 20 faces up and the posture of the support portion 29 is adjusted to a state where the radiation irradiation unit 24 is positioned over the imaging surface 20. In a case where the imaging posture that has been designated in the posture information is MLO imaging, as shown in FIG. 3, the posture of the holding portion 28 is adjusted to a state where the object table 22 has been rotated 45° or more and less than 90° and the posture of the support portion 29 is adjusted to a state where the radiation irradiation unit 24 is positioned over the imaging surface 20.

In the radiographic imaging apparatus 10, stereo imaging is performed individually with respect to the right and left breasts N of each subject W.

When imaging is performed, the subject W rests either one of her right or left breast N on the imaging surface 20 of the radiographic imaging apparatus 10. In the radiographic imaging apparatus 10, when an operation instruction to initiate compression is given with respect to the operation panel 44 in this state, the compression plate 26 moves towards the imaging surface 20. When the compression plate 26 touches and further presses the breast N and the pressing force of the compression plate 26 reaches a set pressing force, the movement of the compression plate 26 is stopped by the control of the imaging apparatus control unit 46.

Figure 8:
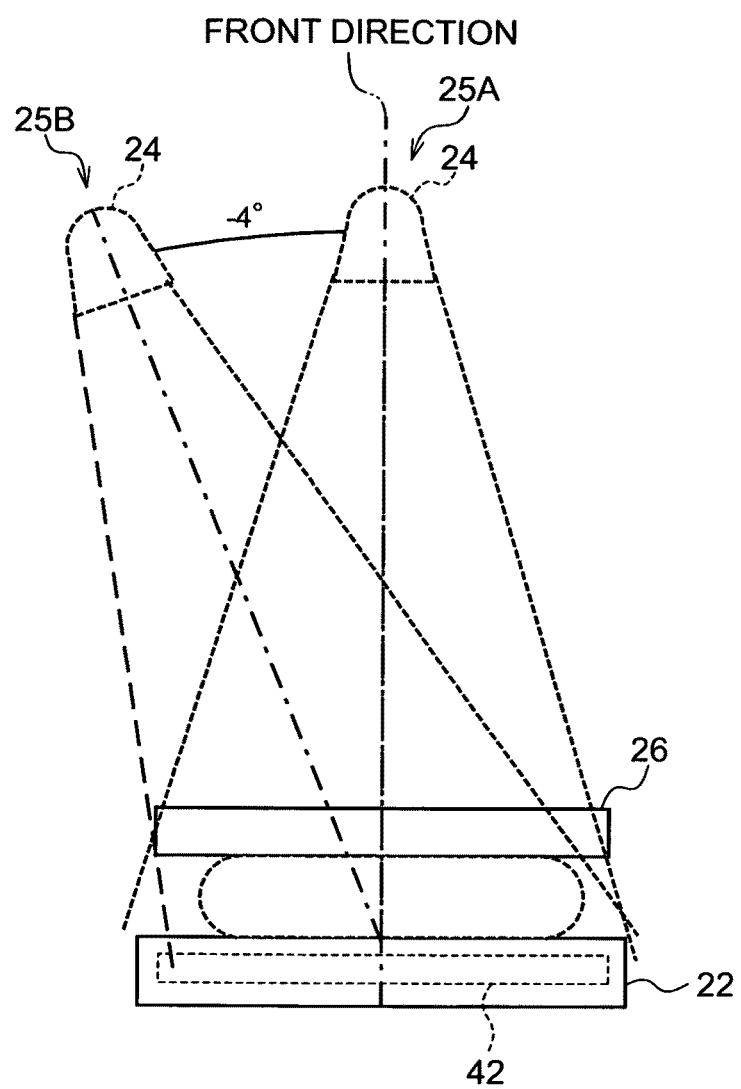
FIG. 8 is a diagram showing positions of a radiation irradiation unit when performing stereo imaging pertaining to a first embodiment.

In the radiographic imaging apparatus 10 pertaining to the present embodiment, when an operation instruction to initiate exposure is given with respect to the operation panel 44 in this state, the grid 40 is reciprocally moved by the moving mechanism 43. As shown in FIG. 8, just the support portion 29 is rotated in the same direction in the case of the right breast and in the case of the left breast, so that the imaging surface 20 is individually irradiated with beams of radiation from the radiation source 30 of the radiation irradiation unit 24 in a position 25A that becomes a front direction in which the radiation irradiation unit 24 directly faces the imaging surface 20 and in a position 25B of a predetermined angle (e.g., −4°) with respect to the front direction. This predetermined angle may be a fixed value or may also, for example, be changed depending on the imaging target site, the lesion part to be observed, the thickness of the imaging target site, and so forth. The beams of radiation with which the breast N has been separately irradiated from the radiation irradiation unit 24 are transmitted through the breast N and reach the radiation detector 42.

When the imaging surface 20 is irradiated with the beams of radiation, the radiation detector 42 outputs to the imaging apparatus control unit 46 sets of image information representing the radiographic images that have been captured.

Figure 9:
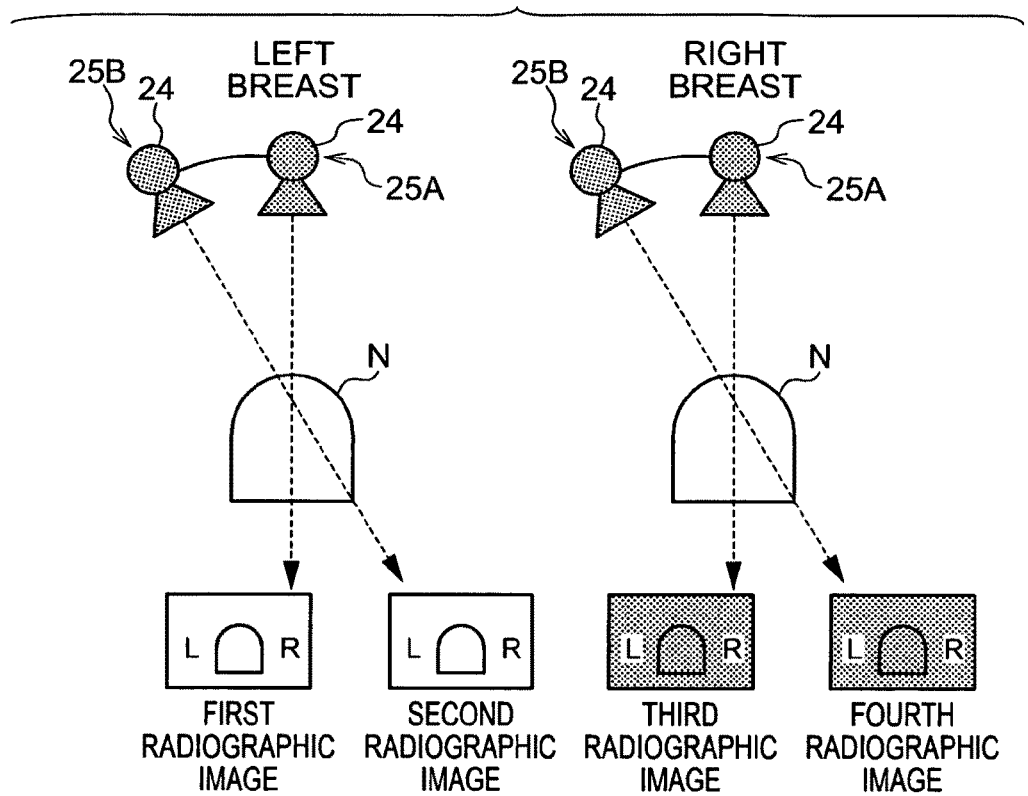
FIG. 9 is a diagram showing the relationship between the positions of the radiation irradiation unit and radiographic images when stereo-imaging a right breast and a left breast pertaining to the first embodiment.

In the radiographic imaging apparatus 10, when imaging with respect to either one of the right or left breast N of the subject W is completed, the same stereo imaging is also performed with respect to the other breast N. Hereinafter, in order to distinguish between the four radiographic images in which the right breast and the left breast have been captured as imaging targets, as shown in FIG. 9, the radiographic image that has been captured as a result of the left breast being irradiated with a beam of radiation from the position 25A will be called a first radiographic image, the radiographic image that has been captured as a result of the left breast being irradiated with a beam of radiation from the position 25B will be called a second radiographic image, the radiographic image that has been captured as a result of the right breast being irradiated with a beam of radiation from the position 25A will be called a third radiographic image, and the radiographic image that has been captured as a result of the right breast being irradiated with a beam of radiation from the position 25B will be called a fourth radiographic image. "L" and "R" added to each radiographic image represent left (L) and right (R) in the image at the time of imaging. In the present embodiment, the first radiographic image and the third radiographic image are of better image quality than the second radiographic image and the fourth radiographic image because they are captured as a result of the imaging surface 20 being irradiated with beams of radiation from the front direction.

The imaging apparatus control unit 46 transmits to the image processing device 50 by communication sets of image information representing a total of four radiographic images (the first to fourth radiographic images) in which the right and left breasts N have been captured per subject W.

The image processing device 50 performs various types of image correction processing such as shading compensation with respect to the sets of image information that have been received by the communication I/F unit 72 and stores the sets of image information after correction in the HDD 66 as sets of imaging information that have been obtained by one-time imaging with respect to the subject W.

The image processing device 50 is configured such that it can have the stereo display device 80 display in parallel the radiographic images of the right and left breasts side-by-side such that their chest wall sides face each other to compare the right and left breasts. When a predetermined operation instruction instructing parallel display of the right and left breasts is given with respect to the operation input unit 54, the image processing device 50 performs image synthesis processing, which synthesizes the radiographic images of the right and left breasts such that their chest wall sides face each other, and has the stereo display device 80 display stereo images in which the radiographic images have been synthesized.

Figure 10:
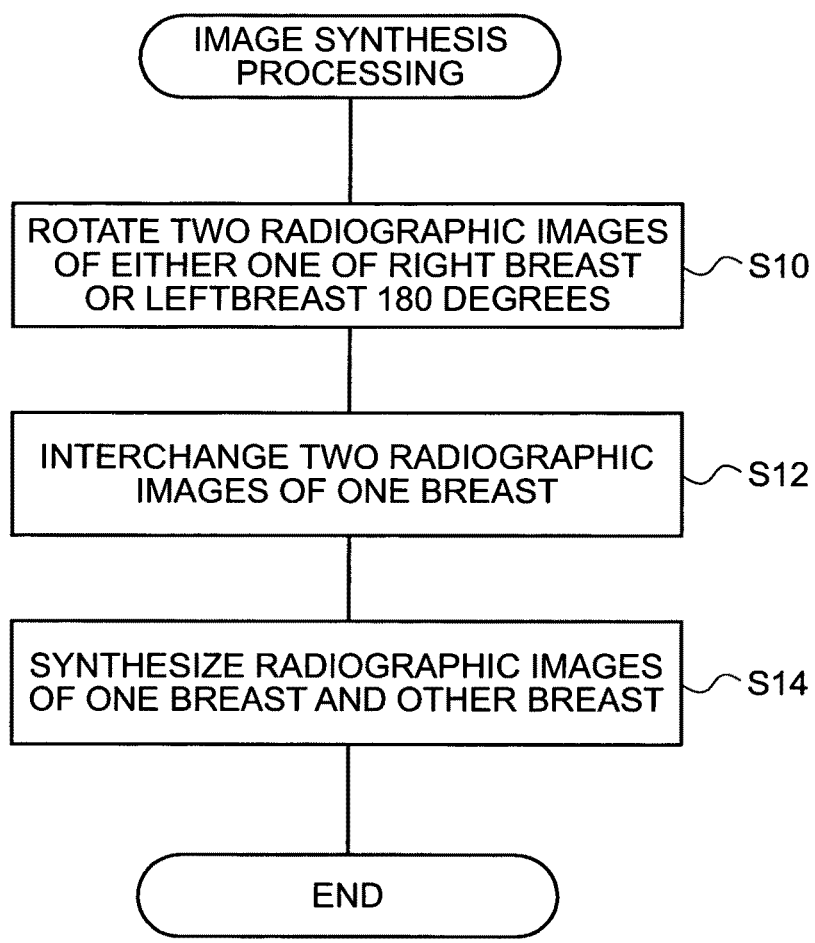
FIG. 10 is a flowchart showing a flow of processing by an image synthesis processing program pertaining to the embodiments.

FIG. 10 is a flowchart showing a flow of processing by an image synthesis processing program that is executed by the CPU 60 pertaining to the present embodiment. This program is stored beforehand in a predetermined region of the ROM 62.

In step S10 of FIG. 10, the two radiographic images (the first and second radiographic images or the third and fourth radiographic images) of either one of the right breast or the left breast of the subject W that have been stored as a set of imaging information in the HDD 66 are rotated 180 degrees.

In the next step S12, the two radiographic images that have been rotated in step 10 are mutually interchanged to reverse the images viewed by the right eye and the left eye.

In the next step S14, the two radiographic images of the one breast that have been interchanged in step S12 and the two radiographic images of the other breast are synthesized such that the edges on the chest sides thereof are brought together, the synthesized images in which the radiographic images have been synthesized are stereo-displayed, and the processing ends.

Figure 11:
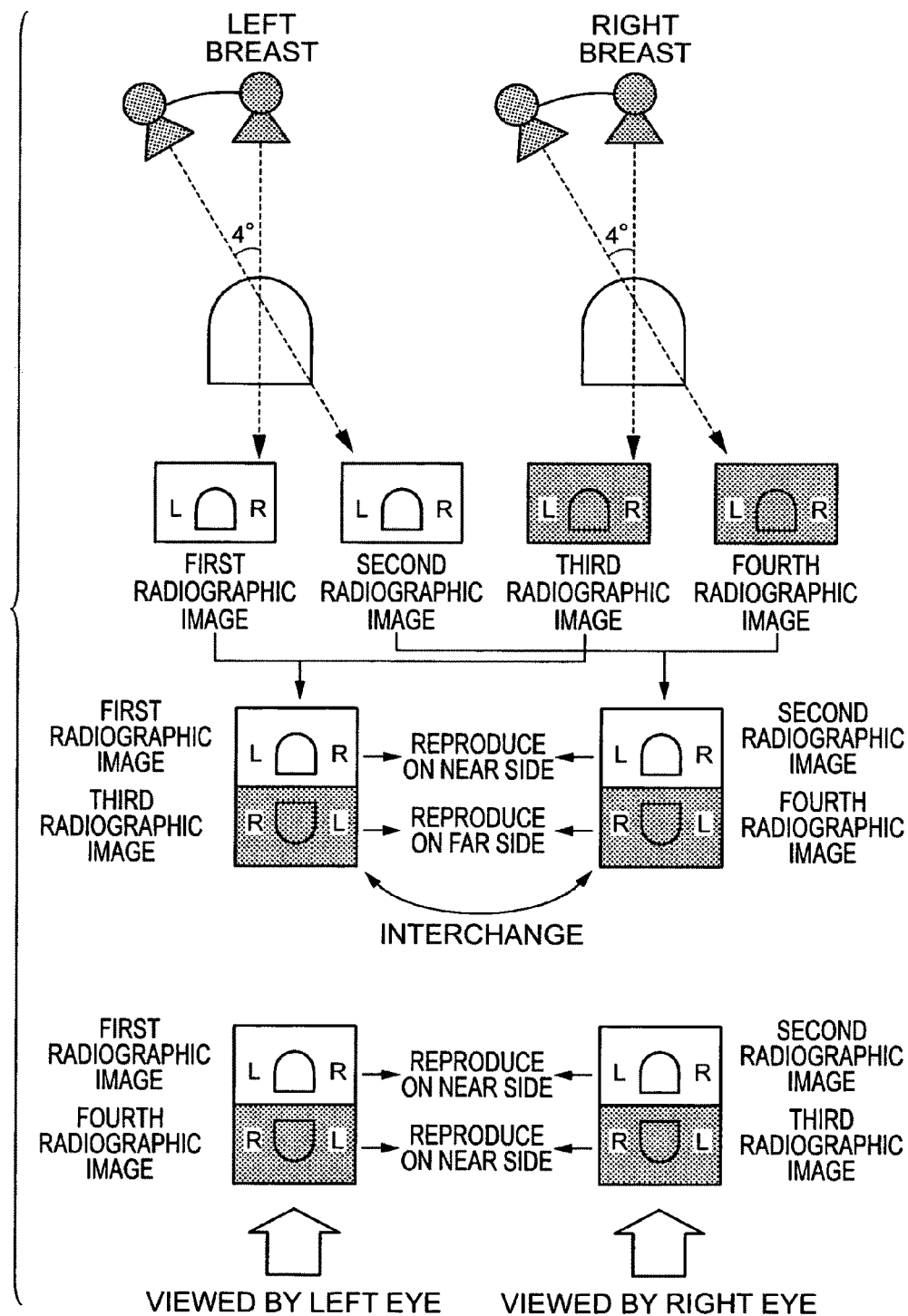
FIG. 11 is a schematic diagram showing a flow of the image synthesis processing pertaining to the first embodiment.

Thus, it is possible for a reader such as a doctor to read the radiographic images and make a diagnosis. FIG. 11 schematically shows a flow of the image synthesis processing pertaining to the present embodiment.

In FIG. 11, the third and fourth radiographic images of the right breast are rotated 180 degrees.

If the third radiographic image that has been rotated 180 degrees is synthesized with the first radiographic image and the fourth radiographic image that has been rotated 180 degrees is synthesized with the second radiographic image, the directions in which the right breast and the left breast project end up becoming opposite in the stereoscopically viewed images.

In step S12, the two radiographic images of the right breast (the third radiographic image and the fourth radiographic image) are mutually interchanged so that the images viewed by the right eye and the left eye are reversed.

Thus, the directions in which the right breast and the left breast project are the same in the stereoscopically viewed images.

By wearing the polarization glasses 85 and viewing the stereo display device 80, the reader can stereoscopically perform a comparison between the right breast and the left breast.

In this manner, according to the present embodiment, in a case where the radiographic imaging apparatus 10 performs stereo imaging, the imaging surface 20 is irradiated with beams of radiation from the front direction in which the radiation irradiation unit 24 directly faces the imaging surface 20 and from the direction of the predetermined angle with respect to the front direction, and radiographic images are captured. In a case where a reader stereoscopically views the radiographic images that have been captured by stereo imaging, there is little image quality deterioration in the radiographic images that have been captured from the front direction, so the right and left breasts N can be stereoscopically observed while image quality deterioration when the radiographic images are stereoscopically viewed is suppressed.

According to the present embodiment, the two radiographic images in which either one of the right breast or the left breast has been captured by stereo imaging are rotated 180 degrees, and these two radiographic images are mutually interchanged and synthesized side-by-side with the two radiographic images in which the other breast has been captured by stereo imaging such that their chest sides are brought together. The directions in which the right breast and the left breast project are the same in the stereoscopically viewed images, so it is easier to perform a comparison between the right breast and the left breast.

Second Embodiment

Next, a second embodiment will be described.

The configurations of the radiographic imaging apparatus 10 and the radiographic imaging system 5 pertaining to the second embodiment are the same as those in the first embodiment (see FIG. 1 to FIG. 7), so description here will be omitted.

Figure 12:
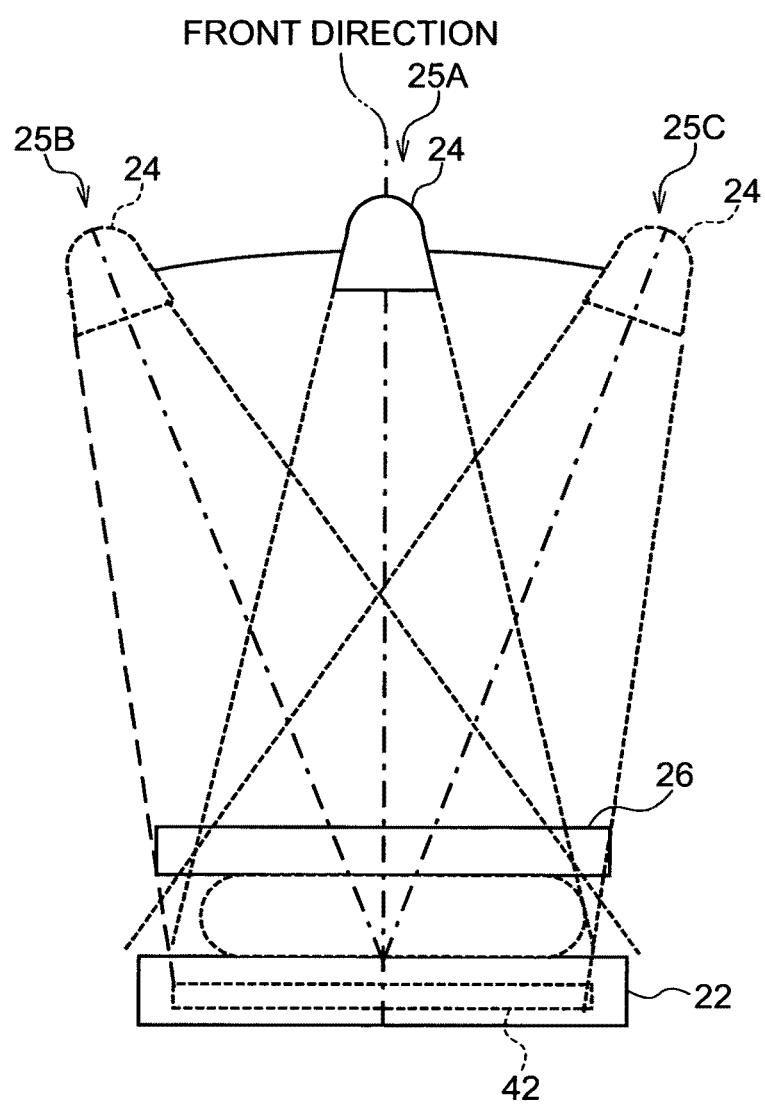
FIG. 12 is a diagram showing positions of the radiation irradiation unit when performing stereo imaging pertaining to a second embodiment.
Figure 13:
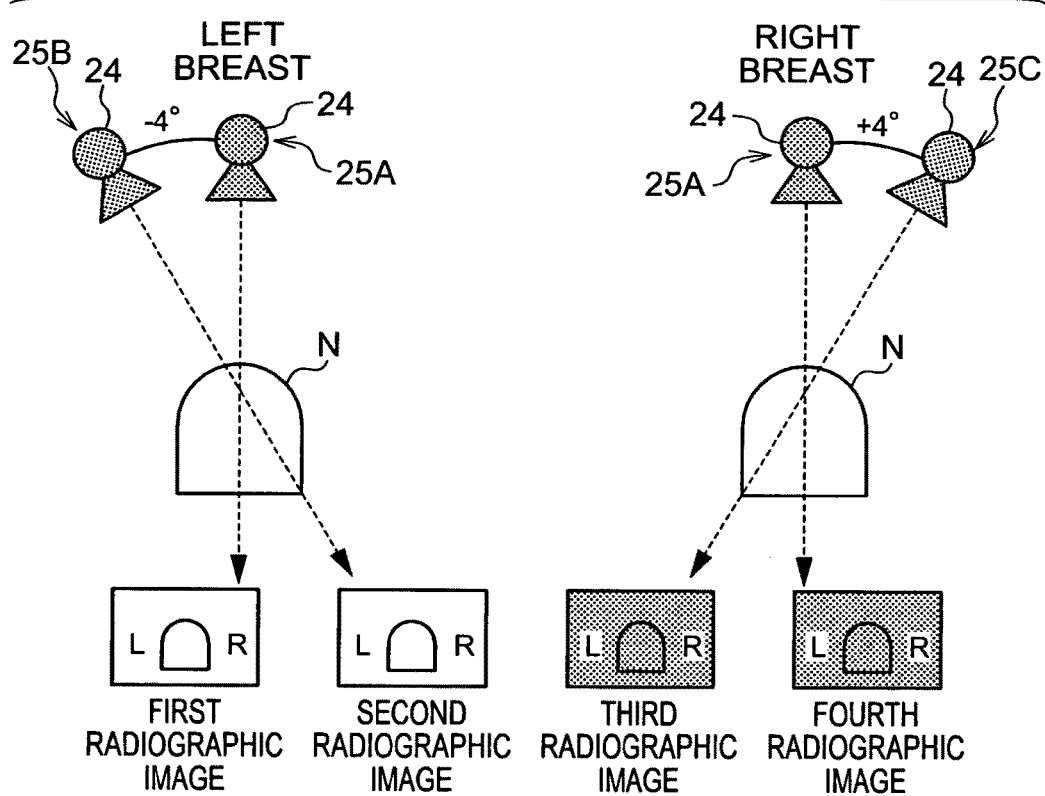
FIG. 13 is a diagram showing the relationship between the positions of the radiation irradiation unit and radiographic images when stereo-imaging a right breast and a left breast pertaining to the second embodiment.

In the radiographic imaging apparatus 10 pertaining to the present embodiment, as shown in FIG. 12, the support portion 29 is rotated in opposite directions in the case of the right breast and in the case of the left breast so that, in the case of the left breast, the imaging surface 20 is individually irradiated with beams of radiation from the radiation source 30 of the radiation irradiation unit 24 in a position 25A that is a front direction in which the radiation irradiation unit 24 directly faces the imaging surface 20 and in a position 25B of a predetermined angle (e.g., −4°) with respect to the front direction and so that, in the case of the right breast, the imaging surface 20 is individually irradiated with beams of radiation from the radiation source 30 of the radiation irradiation unit 24 in the position 25A and in a position 25C of a predetermined angle (e.g., +4°) oppositely from the case of the right breast with respect to the front direction. Hereinafter, in order to distinguish between the four radiographic images in which the right breast and the left breast have been captured as imaging targets, as shown in FIG. 13, the radiographic image that has been captured as a result of the left breast being irradiated with a beam of radiation from the position 25A will be called a first radiographic image, the radiographic image that has been captured as a result of the left breast being irradiated with a beam of radiation from the position 25B will be called a second radiographic image, the radiographic image that has been captured as a result of the right breast being irradiated with a beam of radiation from the position 25C will be called a third radiographic image, and the radiographic image that has been captured as a result of the right breast being irradiated with a beam of radiation from the position 25A will be called a fourth radiographic image. "L" and "R" added to each radiographic image represent left (L) and right (R) in the image at the time of imaging. In the present embodiment, the first radiographic image and the fourth radiographic image are of better image quality than the second radiographic image and the third radiographic image because they are captured as a result of the imaging surface 20 being irradiated with beams of radiation from the front direction.

In a case where the same image synthesis processing as in the first embodiment has been performed with respect to the total of four radiographic images (the first to fourth radiographic images) in which the right and left breasts N have each been captured in this manner, stereo images in which the radiographic images have been synthesized are displayed on the stereo display device 80.

When a predetermined operation instruction instructing parallel display of the right and left breasts is given with respect to the operation input unit 54, the image processing device 50 performs the image synthesis processing of the first embodiment with respect to the radiographic images of the right and left breasts that have been captured in this manner and has the stereo display device 80 display the stereo images in which the radiographic images have been synthesized.

Figure 14:
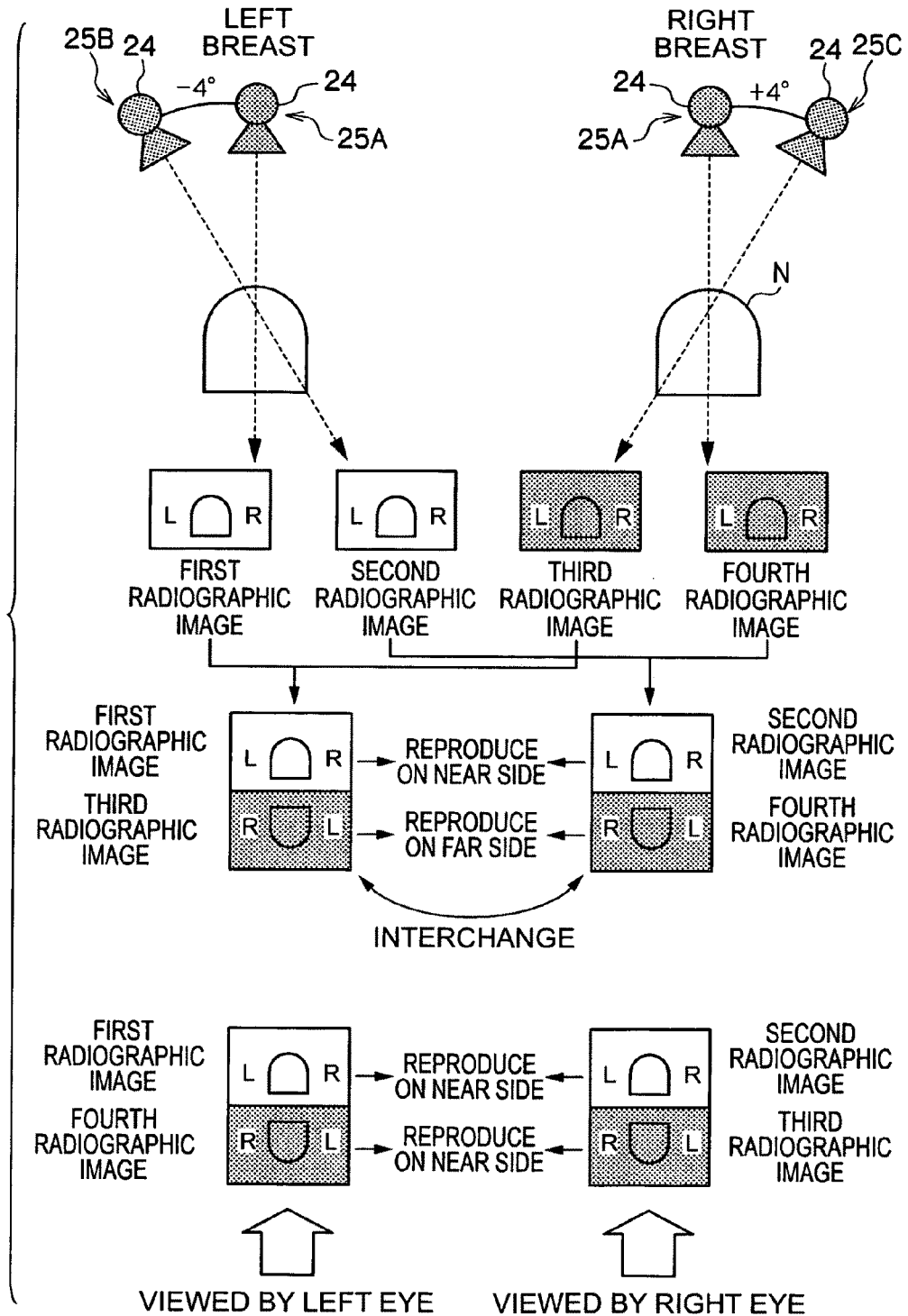
FIG. 14 is a schematic diagram showing a flow of the image synthesis processing pertaining to the second embodiment.

FIG. 14 schematically shows a flow of the image synthesis processing pertaining to the present embodiment.

In FIG. 14, the third and fourth radiographic images of the right breast are rotated 180 degrees and are also mutually interchanged to thereby reverse the images viewed by the right eye and the left eye.

Thus, the directions in which the right breast and the left breast project are the same in the stereoscopically viewed images.

In the present embodiment, the first radiographic image and the fourth radiographic image that have been captured as a result of the imaging surface 20 being irradiated with beams of radiation from the front direction are synthesized, and the second radiographic image and the third radiographic image that have been captured as a result of the imaging surface 20 being irradiated with beams of radiation at the predetermined angles with respect to the front direction are synthesized.

In this manner, according to the present embodiment, the predetermined angles are made symmetrical with respect to the front direction when imaging the right breast and when imaging the left breast, so that when two radiographic images in which either one of the right breast or the left breast has been captured by stereo imaging are rotated 180 degrees, are mutually interchanged, and are synthesized side-by-side with the two radiographic images in which the other breast has been captured by stereo imaging such that their chest sides meet, the radiographic images that have been captured as a result of the imaging surface 20 being irradiated with beams of radiation from the front direction (the first radiographic image and the fourth radiographic image) are synthesized; thus, it becomes difficult to feel the difference in the image qualities of the radiographic images in the synthesized images.

In the above embodiments, a case where the radiographic imaging apparatus 10 is applied to radiographic images captured by mammography has been described, but the present invention is not limited to this and may also be applied to other radiographic imaging apparatus.

In the above embodiments, a case where the radiographic imaging system 5 uses the stereo display device 80 in which the two display units 82 are placed vertically side-by-side has been described, but the present invention is not limited to this. For example, the present invention may also be configured to separately display an image for the right eye and an image for the left eye in odd lines and in even lines of a single display unit whose display light polarization directions are orthogonal in the odd lines and in the even lines. The present invention may also be configured such that the displayed colors are changed in the image for the right eye and in the image for the left eye so that the radiographic images are stereoscopically viewed using glasses that transmit different colors in the right lens and in the left lens. The present invention may also be configured such that the image for the right eye and the image for the left eye are alternately displayed in time divisions on a single display unit so that the radiographic images are stereoscopically viewed using glasses that alternately block the right lens and the left lens in accordance with the time division display of the display unit.

In the above embodiments, a case where sets of digital image information representing radiographic images are directly obtained by the radiation detector 42 has been described, but the present invention is not limited to this. For example, the present invention may also be configured such that the digital image information is obtained by irradiating a cassette or the like housing an imaging plate or X-ray film with radiation and reading the imaging plate or X-ray film housed in the cassette.

The configurations of the radiographic imaging system 5, the radiographic imaging apparatus 10, the image processing device 50, and the stereo display device 80 described in the above embodiments (see FIG. 1 to FIG. 5) are examples and, it goes without saying, can be altered depending on the situation in a scope that does not depart from the gist of the present invention.

The flow of the processing by the image synthesis processing program described in the above embodiments (see FIG. 10) is also an example and, it goes without saying, can be altered depending on the situation in a scope that does not depart from the gist of the present invention.

Embodiments of the present invention are described above, but the present invention is not limited to the embodiments as will be clear to those skilled in the art.

What is claimed is:

1. A radiographic imaging apparatus comprising:
   a radiation detector that captures radiographic images based on beams of radiation that have been transmitted through an imaging target site and with which an imaging surface has been individually irradiated and generates sets of image information representing the captured radiographic images;
   a radiation source that irradiates the imaging surface with the beams of radiation;
   a moving unit that moves the radiation source such that irradiation with the beams of radiation is possible from different directions including a front direction in which the radiation source directly faces the imaging surface; and
   an imaging control unit that controls the moving unit such that, in a case where the radiographic imaging apparatus performs stereo imaging, the imaging surface is irradiated with the beams of radiation from the front direction and from a direction of a predetermined angle with respect to the front direction,
   wherein the imaging target site is breasts, and
   wherein the imaging control unit sets the predetermined angle in opposite directions with respect to the front direction when imaging a right breast and when imaging a left breast.

2. The radiographic imaging apparatus according to claim 1,
   wherein in a case where the radiographic imaging apparatus performs stereo imaging of the right breast and the left breast, the imaging control unit controls the moving unit such that the imaging surface is irradiated with the beams of radiation from the front direction and from the direction of the predetermined angle, and
   wherein the radiographic imaging apparatus further comprises a display control unit that performs control such that radiographic images in which the right breast and the left breast have been individually stereo-imaged are displayed side-by-side at a display unit such that chest sides of the radiographic images meet, and such that the directions in which the right breast and the left breast project are the same when stereoscopically viewed,
   wherein the display unit displays the radiographic images so as to allow the radiographic images to be viewed individually by a right eye and a left eye such that stereoscopic viewing is possible.

3. The radiographic imaging apparatus according to claim 2, wherein the display control unit performs control such that two radiographic images, in which either one of the right breast or the left breast has been stereo-imaged, are rotated 180 degrees, the two radiographic images are mutually interchanged, and a synthesized image is displayed in which the two radiographic images and two other radiographic images in which the other breast has been stereo-imaged are arranged side-by-side and synthesized such that chest sides of the radiographic images meet.

4. A radiographic imaging apparatus comprising:
   a radiation detector that captures radiographic images based on beams of radiation that have been transmitted through an imaging target site and with which an imaging surface has been individually irradiated and generates sets of image information representing the captured radiographic images;
   a radiation source that irradiates the imaging surface with the beams of radiation;
   a moving unit that moves the radiation source such that irradiation with the beams of radiation is possible from different directions including a front direction in which the radiation source directly faces the imaging surface;
   an imaging control unit that controls the moving unit such that, in a case where the radiographic imaging apparatus performs stereo imaging, the imaging surface is irradiated with the beams of radiation from the front direction and from a direction of a predetermined angle with respect to the front direction,
   wherein the imaging target site is breasts; and the radiographic imaging apparatus further comprises a display control unit, wherein the display control unit performs control such that two radiographic images, in which either one of a right breast or a left breast has been stereo-imaged, are rotated 180 degrees, the two radiographic images are mutually interchanged, and a synthesized image is displayed in which the two radiographic images and two other radiographic images in which the other breast has been stereo-imaged are arranged side-by-side and synthesized such that chest sides of the radiographic images meet.

5. The radiographic imaging apparatus according to claim 4, wherein in a case where the radiographic imaging apparatus performs stereo imaging of the right breast and the left breast, the imaging control unit controls the moving unit such that the imaging surface is irradiated with the beams of radiation from the front direction and from the direction of the predetermined angle, and wherein the display control unit performs control such that radiographic images in which the right breast and the left breast have been individually stereo-imaged are displayed side-by-side at a display unit such that chest sides of the radiographic images meet, and such that the directions in which the right breast and the left breast project are the same when stereoscopically viewed, wherein the display unit displays the radiographic images so as to allow the radiographic images to be viewed individually by a right eye and a left eye such that stereoscopic viewing is possible.

6. A radiographic imaging system comprising:

a. a radiographic imaging apparatus comprising:

a radiation detector that captures radiographic images based on beams of radiation that have been transmitted through an imaging target site and with which an imaging surface has been individually irradiated and generates sets of image information representing the captured radiographic images, a radiation source that irradiates the imaging surface with the beams of radiation, a moving unit that moves the radiation source such that irradiation with the beams of radiation is possible from different directions including a front direction in which the radiation source directly faces the imaging surface, and an imaging control unit that controls the moving unit such that, in a case where the radiographic imaging apparatus performs stereo imaging, the imaging surface is irradiated with the beams of radiation from the front direction and from a direction of a predetermined angle with respect to the front direction;

b. a display device that displays radiographic images so as to allow the radiographic images to be viewed individually by a right eye and a left eye such that stereoscopic viewing is possible; and c. a display control unit that performs control such that radiographic images in which a right breast and a left breast have been individually stereo-imaged are displayed side-by-side such that chest sides of the radiographic images meet, and such that the directions in which the right breast and the left breast project are the same when stereoscopically viewed, wherein the imaging control unit sets the predetermined angle in opposite directions with respect to the front direction when imaging the right breast and when imaging the left breast.

7. A radiographic imaging system comprising:

a. a radiographic imaging apparatus comprising:

a radiation detector that captures radiographic images based on beams of radiation that have been transmitted through an imaging target site and with which an imaging surface has been individually irradiated and generates sets of image information representing the captured radiographic images, a radiation source that irradiates the imaging surface with the beams of radiation, a moving unit that moves the radiation source such that irradiation with the beams of radiation is possible from different directions including a front direction in which the radiation source directly faces the imaging surface, and an imaging control unit that controls the moving unit such that, in a case where the radiographic imaging apparatus performs stereo imaging, the imaging surface is irradiated with the beams of radiation from the front direction and from a direction of a predetermined angle with respect to the front direction;

b. a display device that displays radiographic images so as to allow the radiographic images to be viewed individually by a right eye and a left eye such that stereoscopic viewing is possible; and c. a display control unit that performs control such that radiographic images in which a right breast and a left breast have been individually stereo-imaged are displayed side-by-side such that chest sides of the radiographic images meet, and such that the directions in which the right breast and the left breast project are the same when stereoscopically viewed, wherein the display control unit performs control such that two radiographic images, in which either one of the right breast or the left breast has been stereo-imaged, are rotated 180 degrees, the two radiographic images are mutually interchanged, and a synthesized image is displayed in which the two radiographic images and two other radiographic images in which the other breast has been stereo-imaged are arranged side-by-side and synthesized such that chest sides of the radiographic images meet.

* * * * *